(12) United States Patent
Griffin

(10) Patent No.: US 12,299,490 B2
(45) Date of Patent: May 13, 2025

(54) ADJUSTING MENTAL STATE TO IMPROVE TASK PERFORMANCE AND COACHING IMPROVEMENT

(71) Applicant: Insight Direct USA, Inc., Tempe, AZ (US)

(72) Inventor: Michael Griffin, Wayland, MA (US)

(73) Assignee: Insight Direct USA, Inc., Chandler, AZ (US)

( * ) Notice: Subject to any disclaimer, the term of this patent is extended or adjusted under 35 U.S.C. 154(b) by 414 days.

(21) Appl. No.: 17/951,970

(22) Filed: Sep. 23, 2022

(65) Prior Publication Data

US 2023/0178216 A1   Jun. 8, 2023

Related U.S. Application Data

(60) Provisional application No. 63/405,712, filed on Sep. 12, 2022, provisional application No. 63/405,709, (Continued)

(51) Int. Cl.
*G06F 9/50* (2006.01)
*G06F 40/30* (2020.01)
(Continued)

(52) U.S. Cl.
CPC ............ *G06F 9/5027* (2013.01); *G06F 40/30* (2020.01); *G06N 5/022* (2013.01); *G06V 20/46* (2022.01); *G06V 20/52* (2022.01); *G06V 40/20* (2022.01); *G10L 15/1815* (2013.01); *G10L 25/63* (2013.01); *G16H 20/70* (2018.01); *G16H 50/50* (2018.01)

(58) Field of Classification Search
CPC ....... G06F 9/5027; G06F 40/30; G06N 5/022; G06N 20/10; G06N 3/044; G06N 5/01; G06N 20/00; G06N 3/045; G06N 3/08; G06V 20/46; G06V 20/52; G06V 40/20; G06V 20/41; G06V 10/803; G10L 15/1815; G10L 25/63; G10L 25/51; G16H 20/70; G16H 50/50
USPC ......................................................... 382/128
See application file for complete search history.

(56) References Cited

U.S. PATENT DOCUMENTS 10,154,810 B2 *  12/2018  Tzvieli ................... A61B 5/165
10,573,313 B2 *   2/2020  Mishra ................ G06V 40/172
(Continued)

*Primary Examiner* — Negussie Worku
(74) *Attorney, Agent, or Firm* — Kinney & Lange, P.A.

(57) ABSTRACT

A method of adjusting mental state includes acquiring video data of a first individual, identifying a first set of features based on image, audio, and text data extracted from the video data, predicting a baseline mental state for the first individual based on the first set of features, identifying a target mental state, and simulating a predicted path from the baseline mental state to the target mental state. The predicted path is simulated using a multidimensional mental state model, a plurality of actions, and a computer-implemented machine learning model. The predicted path comprises one or more actions of the plurality of actions and corresponding changes to at least one of first and second dimensions of the multidimensional mental state model. The one or more actions of the predicted path are output to a second individual and are performable to adjust the baseline mental state of the first individual.

20 Claims, 7 Drawing Sheets

Related U.S. Application Data filed on Sep. 12, 2022, provisional application No. 63/405,714, filed on Sep. 12, 2022, provisional application No. 63/405,724, filed on Sep. 12, 2022, provisional application No. 63/286,844, filed on Dec. 7, 2021.

(51) Int. Cl.

| | |
|---|---|
| *G06N 5/022* | (2023.01) |
| *G06V 20/40* | (2022.01) |
| *G06V 20/52* | (2022.01) |
| *G06V 40/20* | (2022.01) |
| *G10L 15/18* | (2013.01) |
| *G10L 25/63* | (2013.01) |
| *G16H 20/70* | (2018.01) |
| *G16H 50/50* | (2018.01) |

(56) References Cited

U.S. PATENT DOCUMENTS

| | | | |
|---|---|---|---|
| 2016/0022193 A1* | 1/2016 | Rau | G16H 40/67 |
| | | | 600/595 |
| 2021/0194985 A1* | 6/2021 | Gilbert | A61B 5/024 |
| 2022/0020464 A1* | 1/2022 | Zivkovic | G06F 18/2413 |
| 2023/0178098 A1* | 6/2023 | Griffin | G06V 20/41 |
| | | | 382/116 |
| 2023/0252315 A1* | 8/2023 | Griffin | G06N 3/08 |
| | | | 706/12 |
| 2024/0120049 A1* | 4/2024 | Griffin | G16H 10/60 |

* cited by examiner

ADJUSTING MENTAL STATE TO IMPROVE TASK PERFORMANCE AND COACHING IMPROVEMENT

CROSS-REFERENCE TO RELATED APPLICATION(S)

This application claims the benefit of U.S. Provisional Application No. 63/286,844 filed Dec. 7, 2021 for "MACHINE LEARNING METHOD TO QUANTIFY PRESENT STATE-OF-MIND AND PREDICT FUTURE STATE-OF-MIND OF ONE OR MORE INDIVIDUALS BASED ON VIDEO IMAGES OF THOSE INDIVIDUALS" by M. Griffin, H. Kotvis, K. Lumb, K. Poulson, and J. Miner, the disclosure of which is incorporated in its entirety by reference herein; of U.S. Provisional Application 63/405,724 filed Sep. 12, 2022 for "TASK PERFORMANCE ADJUSTMENT BASED ON VIDEO ANALYSIS" by M. Griffin, the disclosure of which is incorporated in its entirety by reference herein; of U.S. Provisional Application 63/405,709 filed Sep. 12, 2022 for "ADJUSTING MENTAL STATE TO IMPROVE TASK PERFORMANCE" by M. Griffin, the disclosure of which is incorporated in its entirety by reference herein; of U.S. Provisional Application 63/405,712 filed Sep. 12, 2022 for "ADJUSTING MENTAL STATE TO IMPROVE TASK PERFORMANCE AND COACHING IMPROVEMENT" by M. Griffin, the disclosure of which is incorporated in its entirety by reference herein; and of U.S. Provisional Application 63/405,714 filed Sep. 12, 2022 for "ADJUSTING MENTAL STATE TO IMPROVE TASK PERFORMANCE AND COACHING IMPROVEMENT" by M. Griffin, the disclosure of which is also incorporated in its entirety by reference herein.

BACKGROUND

The present disclosure relates to mental state adjustment and, more particularly, systems and methods for predicting and adjusting mental state using video data.

Individuals convey information through multiple ways, including verbal and non-verbal means. In conversational or social interactions, interpreting verbal and non-verbal information simultaneously and in real-time can be difficult. Further, some individuals have impairments or disabilities that can significantly increase the difficulty of interpreting verbal and/or non-verbal information.

SUMMARY

An embodiment of a method of adjusting mental state according to the present disclosure includes acquiring video data of a first individual, extracting image data and audio data from the video data, extracting semantic text data from the audio data, identifying a first set of features, predicting a baseline mental state of the first individual, identifying a target mental state for the first individual, simulating a predicted path from the baseline mental state to the target mental state, and outputting an indication of one or more actions to a second individual. The first set of features are identified by analyzing at least one of the image data, the audio data, and the semantic text data. The baseline mental state is predicted based on the first set of features and comprises a first mental state value and a second mental state value. The first mental state value corresponds to a first dimension of a multidimensional mental state model and the second mental state value corresponds to a second dimension of the multidimensional mental state model. The target mental state comprises a third mental state value and a fourth mental state value. The third mental state value corresponds to the first dimension of the multidimensional mental state model and the fourth mental state value corresponds to the second dimension of the multidimensional mental state model. The predicted path is simulated by a simulator and is simulated using the multidimensional mental state model, a plurality of actions, and a first computer-implemented machine learning model. The first computer-implemented machine learning model is configured to relate actions of the plurality of actions and changes in value in at least one of the first dimension and the second dimension of the multidimensional mental state model. The predicted path comprises one or more actions of the plurality of actions and corresponding changes to at least one of the first dimension and the second dimension of the multidimensional mental state model and the one or more actions are performable by the individual. The one or more actions output to the second individual are the one or more actions of the predicted path. The one or more actions are performable by the second individual to adjust the baseline mental state of the first individual toward the target mental state.

An embodiment of a system for adjusting mental state according to the present disclosure includes processor, a user interface, and memory. The user interface is configured to enable an operator to interact with the processor. The memory is encoded with instructions that, when executed, cause the processor to acquire video data of a first individual, extract image data and audio data from the video data, extract semantic text data from the audio data, and analyze at least one of the image data, the audio data, and the semantic text data to identify a first set of features. The instructions further cause the processor to predict a baseline mental state of the first individual based on the first set of features, identify a target mental state for the first individual, and simulate a predicted path from the baseline mental state toward the target mental state. The baseline mental state comprises a first mental state value and a second mental state value, the first mental state value corresponds to a first dimension of a multidimensional mental state model, and the second mental state value corresponds to a second dimension of the multidimensional mental state model. The target mental state comprises a third mental state value and a fourth mental state value, the third mental state value corresponds to the first dimension of the multidimensional mental state model, and the fourth mental state value corresponds to the second dimension of the multidimensional mental state model. The predicted path is simulated by a simulator using the multidimensional mental state model, a plurality of actions, and a first computer-implemented machine learning model. The first computer-implemented machine learning model is configured to relate actions of the plurality of actions and changes in value in at least one of the first dimension and the second dimension of the multidimensional mental state model, the predicted path comprises one or more actions of the plurality of actions and corresponding changes to at least one of the first dimension and the second dimension of the multidimensional mental state model, and the one or more actions are performable by a second individual to adjust the baseline mental state of the first individual toward the target mental state. The instructions also cause the processor to cause the user interface to output an indication of the one or more actions to the second individual.

DETAILED DESCRIPTION

Figure 1:
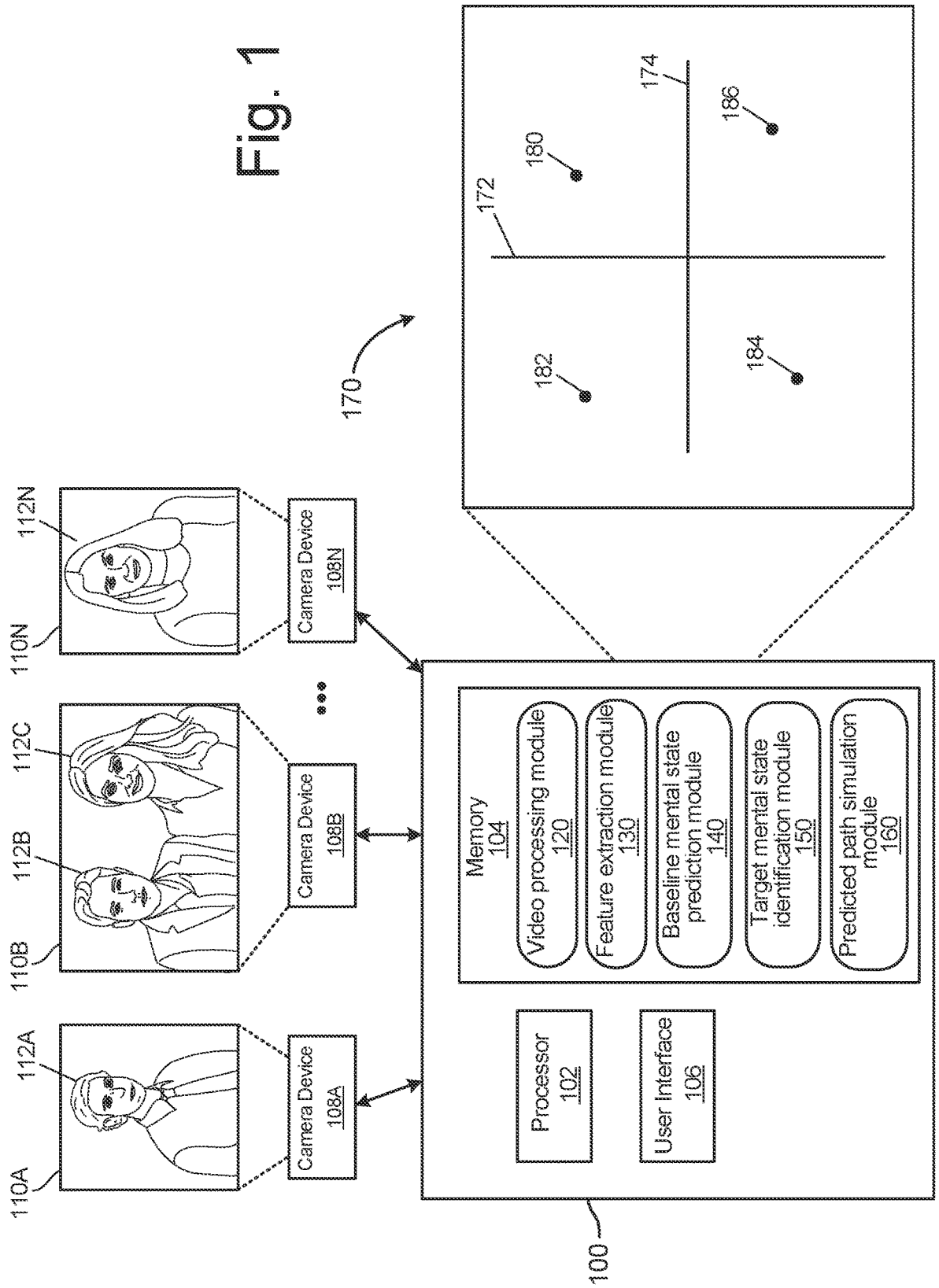
FIG. 1 is a schematic view of an example of a mental state adjuster.

The present disclosure relates to systems and methods for adjusting a state of mind of an individual captured in video data. More specifically, the present disclosure relates to systems and methods for predicting state of mind for the individual and for predicting a set of actions for another, second individual to adjust the state of mind of the individual captured in the video data. As will be explained in more detail subsequently, the systems and methods disclosed herein allow for prediction of a baseline mental state using a multidimensional mental state model that assigns different aspects of mental state to different dimensions of the model, thereby significantly improving the resolution and accuracy of mental state predictions as compared to existing models of mental state. Further, the methods and systems disclosed herein enable the prediction of a series of actions that can be performed by another, second individual interacting with the first individual for whom a baseline mental state was predicted. The actions are selected to adjust the first individual's baseline mental state to a target mental state associated with improved task performance.

As used herein, "mental state" refers to the attitude, mood, and/or emotion of an individual. The mental state of an individual can be significantly more complex than, for example, an emotion of the individual. Existing methods can use video data to identify discrete emotions and are not capable of identifying more complex mental states. As will be explained in substantially more detail subsequently, the multidimensional mental state models described herein advantageously are able to distinguish and identify an individual's mental state, as opposed to simply identifying the individual's emotion. For example, existing methods focused on emotion may be limited to simple emotional states such as "happy," "sad," "neutral," or "afraid," while a multidimensional mental state model according to the present disclosure can be used to identify more complex mental states, such as "bored," "satisfied," "sleepy," or "content" in addition to the emotional states identifiable by simpler existing methods.

Further, the multidimensional mental state models described herein allow for mental state to be determined based on the extent to which an individual is experiencing various mental state components that contribute to an overall mental state. For example, it is possible for an individual to be simultaneously or substantially simultaneously experiencing two or more emotions, attitudes, and/or moods in varying degrees. Each emotion, attitude, and/or mood can be described by a dimension of the multidimensional mental state model, allowing the individual's overall mental state to be determined with significantly more accuracy and granularity than existing methods that use a single emotion, attitude, and/or mood to describe mental state.

Current methods of estimating individual attitude or emotion specialize in extremely narrow use cases (e.g., analyzing the alertness of automobile drivers or eye-tracking to gauge a person's attention level). Notably, as the methods herein are configured to use of a multidimensional mental state model rather than a simpler, existing emotion model, the systems and methods disclosed herein can be applied to a wide variety of applications and use cases, reducing the need for the development of use-case specific models to understand mental state. The use of a multidimensional mental state model also allows the methods for predicting actions for adjusting mental state to be adapted to a wide variety of applications and use cases, also reducing the need for development of use-case specific models for understanding changes to mental state.

As will be explained in more detail, the present disclosure uses mental state predicted from video data of a first individual to predict a series of actions that can be performed by a second individual to adjust the first individual's mental state from a baseline point to a target mental state. The target mental state is an ideal mental state for performing a particular task. Advantageously, this allows for an individual to improve task performance without requiring that the individual simply emulate the behaviors of an individual proficient in the task. Rather, the second individual is able to perform actions that adjust mental state of the first individual to one associated with improved task performance. The systems and methods described herein can be used and adapted for any target mental state, enabling the systems and methods described herein to be used to improve performance of a large variety of tasks and/or activities.

Further, the present disclosure provides methods that can be performed using computer-implemented machine learning models to provide real-time analysis of mental state predictions and real-time prediction of actions for adjusting mental state. Advantageously, this allows for the predicted actions for adjusting the predicted, baseline mental state to be performed by the other, second individual shortly after or during the performance of the task for which the baseline mental state was predicted.

The methods disclosed herein for adjusting mental state are useful for improving performance coaching and related tasks. For example, the methods disclosed herein can improve the performance of an individual at teaching, lecturing, tutoring, performance coaching, or a similar task. Advantageously, the methods disclosed herein enable an individual in a coaching-type role to improve the mental state of another individual in a trainee-type role. The mental state of the individual in the trainee-type role can be improved to, for example, be more receptive to coaching or improvement recommendations from the individual in the coaching-type role. Coaching-type roles can include, for example, teaching, coaching, tutoring, and/or mentoring roles, among other options. Trainee-type roles can include, for example, student, trainee, tutee, and/or mentee roles, among other options.

FIG. 1 is a schematic diagram of mental state adjuster 100, which is a system for generating mental state adjustment information. Mental state adjuster 100 includes processor 102, memory 104, and user interface 106, and is connected to camera devices 108A-N. Camera devices 108A-N capture video data 110A-N of individuals 112A-N. Memory 104 includes video processing module 120, feature extraction module 130, baseline mental state prediction module 140, target mental state identification module 150, and predicted path simulation module 160. Memory 104 also stores multidimensional mental state model 170, which includes first dimension 172, second dimension 174, first point 180, second point 182, third point 184, and fourth point 186.

Processor 102 can execute software, applications, and/or programs stored on memory 104. Examples of processor 102 can include one or more of a processor, a microprocessor, a controller, a digital signal processor (DSP), an application specific integrated circuit (ASIC), a field-programmable gate array (FPGA), or other equivalent discrete or integrated logic circuitry. Processor 102 can be entirely or partially mounted on one or more circuit boards.

Memory 104 is configured to store information and, in some examples, can be described as a computer-readable storage medium. Memory 104, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 104 is a temporary memory. As used herein, a temporary memory refers to a memory having a primary purpose that is not long-term storage. Memory 104, in some examples, is described as volatile memory. As used herein, a volatile memory refers to a memory that that the memory does not maintain stored contents when power to the memory 104 is turned off. Examples of volatile memories can include random access memories (RAM), dynamic random access memories (DRAM), static random access memories (SRAM), and other forms of volatile memories. In some examples, the memory is used to store program instructions for execution by the processor. The memory, in one example, is used by software or applications running on mental state adjuster 100 (e.g., by a computer-implemented machine learning model or a data processing module) to temporarily store information during program execution.

Memory 104, in some examples, also includes one or more computer-readable storage media. Memory 104 can be configured to store larger amounts of information than volatile memory. Memory 104 can further be configured for long-term storage of information. In some examples, memory 104 includes non-volatile storage elements. Examples of such non-volatile storage elements can include, for example, magnetic hard discs, optical discs, floppy discs, flash memories, or forms of electrically programmable memories (EPROM) or electrically erasable and programmable (EEPROM) memories.

User interface 106 is an input and/or output device and enables an operator to control operation of mental state adjuster 100. For example, user interface 106 can be configured to receive inputs from an operator and/or provide outputs regarding the predicted mental state of a portrayed individual and/or the actions for adjusting that predicted mental state. User interface 106 can include one or more of a sound card, a video graphics card, a speaker, a display device (such as a liquid crystal display (LCD), a light emitting diode (LED) display, an organic light emitting diode (OLED) display, etc.), a touchscreen, a keyboard, a mouse, a joystick, or other type of device for facilitating input and/or output of information in a form understandable to users and/or machines.

Mental state adjuster 100 is configured to perform one or more methods described herein. Mental state adjuster 100 can accept data from and/or can be operably connected to an audiovisual data stream and/or an audiovisual data file. Mental state adjuster 100 can use data from an audiovisual data stream and/or an audiovisual data file to determine mental state information. More generally, mental state adjuster 100 is configured to perform any of the functions attributed herein to a mental state adjuster, including receiving an output from any source referenced herein, detecting any condition or event referenced herein, and generating and providing data and information as referenced herein.

Mental state adjuster 100 can be a discrete assembly or be formed by one or more devices capable of individually or collectively implementing functionalities and generating and outputting data as discussed herein. In some examples, mental state adjuster 100 can be implemented as a plurality of discrete circuitry subassemblies. In some examples, mental state adjuster 100 can include or be implemented at least in part as a smartphone or tablet, among other options. In some examples, mental state adjuster 100 and/or user interface 106 of mental state adjuster 100 can include and/or be implemented as downloadable software in the form of a mobile application. The mobile application can be implemented on a computing device, such as a personal computer, tablet, or smartphone, among other suitable devices. Mental state adjuster 100 can be considered to form a single computing device even when distributed across multiple component devices.

Camera devices 108A-N are capable of capturing video data 110A-N of one or more individuals 112A-N. In the depicted example, camera devices 108A and 108N are depicted as capturing video data 110A and 110N of single individuals 112A and 112N. Camera device 108B is depicted as capturing video data 110B of two individuals 112B and 112C. Each camera device 108A-N captures video data 110A-N video of one or more individuals 112A-N. Each camera device 108A-N is configured to be able to communicate with mental state adjuster 100 and mental state adjuster 100 is configured to communicate with each camera device 108A-N. Camera devices 108A-N can be, for example, a video camera, a webcam, or another suitable source for obtaining video data 110A-N. Camera devices 108A-N can be controlled by mental state adjuster 100 or by another suitable video device. Video data 110A-N are audiovisual data feeds portraying individuals 112A-N. Video data 110A-N can be stored to memory 104 for use with one or more methods described herein or can be stored to another storage media and recalled to memory 104 for use with one or more methods described herein.

Although FIG. 1 depicts only three camera devices 108A-N, mental state adjuster 100 can be operatively connected to any number of camera devices 108A-N. Each additional camera device 108A-N can capture video data 110A-N portraying another individual 112A-N. Similarly, although each of video data 110A-N is depicted as portraying a single individual 112A-N, in other examples each of video data 110A-N can depict two or more individuals 112A-N.

Mental state adjuster 100 can use programs of video processing module 120, feature extraction module 130, baseline mental state prediction module 140, target mental state identification module 150, and predicted path simulation module 160 to predict a baseline mental state for a first individual portrayed in video data and to further generate a series of actions that can be performed by a second individual to adjust the mental state of the first individual away from baseline mental state and toward a target mental state. The second individual performs the actions through interaction with the portrayed individual. As will be explained in more detail subsequently, the actions can be, for example, one or more spoken words, one or more hand gestures, or one or more adjustments to vocal tone and/or speaking speed, among other options.

Figure 5:
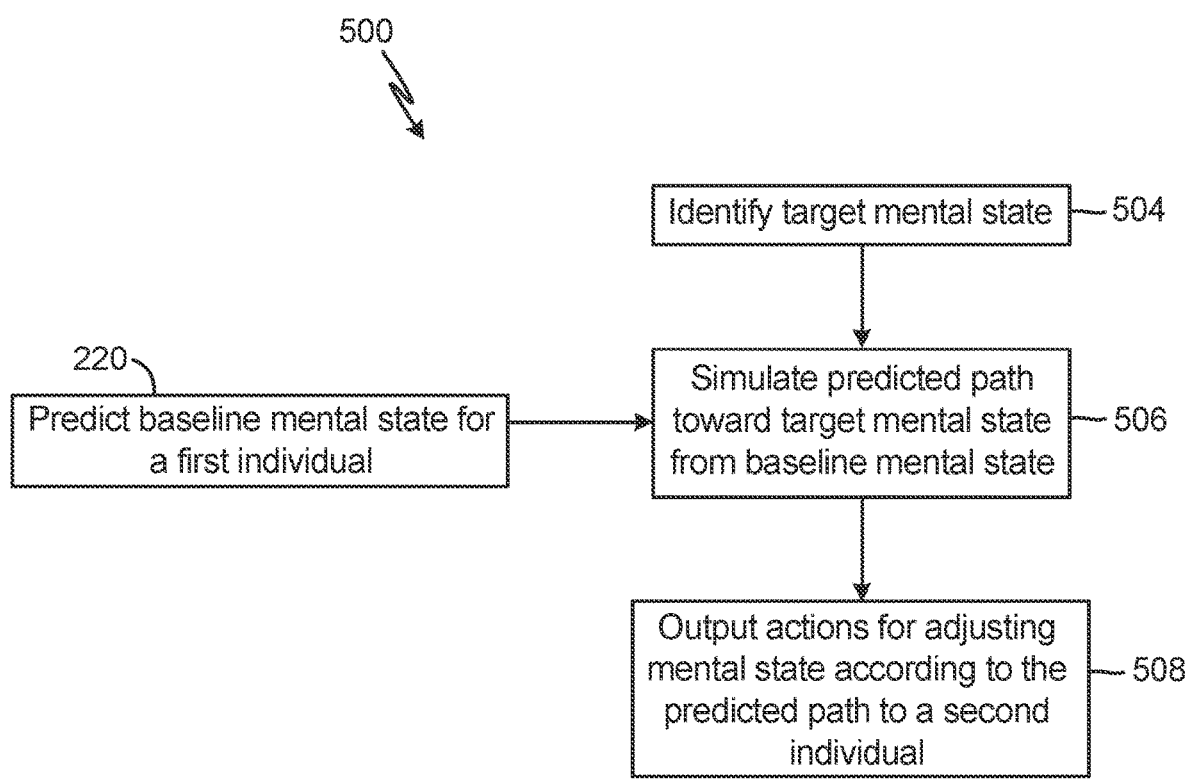
FIG. 5 is a flow diagram of an example of determining actions for adjusting mental state.

As used herein, a "portrayed individual" refers to the first individual portrayed in video data (e.g., one of individuals 112A-N portrayed in video data 110A-N) for which mental state adjustment information is desired. Similarly, as used herein, an "interacting individual" refers to the second individual that is interacting with the portrayed individual and who performs actions to adjust the mental state of the portrayed individual. In some examples, the interacting individual is in a coaching role and the portrayed individual is in a trainee role, such that the interacting individual is coaching the portrayed individual to improve the portrayed individual's performance of a task. The interacting individual is generally more proficient at the task performed by the portrayed individual than the portrayed individual, but the interacting individual is not required to be proficient at skills required for effective coaching or teaching. The interacting individual may also be portrayed in the video data containing the portrayed individual, but video data of the interacting individual is not required to operate mental state adjuster 100 or perform methods 200 (FIG. 2) or 500 (FIG. 5).

Video processing module 120 includes one or more programs for processing video data 110A-N depicting the portrayed individual. For example, video processing module 120 can include one or more programs for extracting image data, audio data, and semantic text data from video data 110A-N. As used herein, "image data" refers to the portion of video data 110A-N that is a series of still images, "audio data" refers to the sound data stored in video data 110A-N, and semantic text data refers to data that represents spoken words, phrases, sentences, and other sounds produced by the portrayed individual as readable text.

Feature extraction module 130 includes one or more programs for classifying the image data, audio data, and semantic text data extracted by video processing module 120. Feature extraction module 130 can include one or more programs for extracting classifiable features from the image data, audio data, and/or semantic text data. In some examples, feature extraction module 130 can include one or more computer-implemented machine learning models for extracting classifiable features from the image data, audio data, and/or semantic text data. The features extracted by feature extraction module 130 are capable of being classified to predict the portrayed individual's mental state and/or to identify the portrayed individual.

Baseline mental state prediction module 140 includes one or more programs for predicting the mental state of the portrayed individual based on the features extracted by feature extraction module 130. In some examples, mental state prediction module 140 can use one or more computer-implemented machine learning models to predict the mental state of the portrayed individual. The mental state predicted by baseline mental state prediction module 140 is the mental state of the portrayed individual as captured in the video data and is used by predicted path simulation module 160 as a starting, baseline mental state for simulating the predicted path toward the target mental state.

Target mental state identification module 150 includes one or more programs for identifying a target mental state for the portrayed individual. The target mental state can be selected based on a task that the portrayed individual is performing or is going to perform. For example, if the individual is performing a studying or learning task, the target mental state can be a focused mental state that will improve the portrayed individual's performance at the studying or learning task. Target mental state identification module 150 can determine the task based on input at user interface 106 or another suitable method.

Predicted path simulation module 160 includes one or more programs for simulating a predicted path from the baseline mental state predicted by baseline mental state prediction module 140 to toward the target mental state identified by target mental state identification module 150. Predicted path simulation module 160 can use one or more computer-implemented machine learning models trained to relate actions performable by the interacting individual to changes in the portrayed individual's mental state (i.e., the mental state predicted using baseline mental state prediction module 140). For example, the one or more computer-implemented machine learning models can be trained to relate changes in one or more dimensions of the portrayed individual's mental state according to a multidimensional mental state model to actions performable by the interacting individual. The actions can be, for example, related and/or specific to a task performed by the interacting individual that causes and/or results in changes to the mental state of the portrayed individual. For example, if the interacting individual is performing a lecture-based task, the actions can be selected to be specific to those actions appropriate for lectures. Similarly, if the interacting individual is performing a demonstration-type task, in which the interacting individual demonstrates proper performance of the task performed by the portrayed individual, the actions can be selected to be those appropriate for demonstrations and/or to better enable the portrayed individual to learn the demonstrated task. The task performed by the interacting individual can be input at user interface 106 and used to select the set of actions used to generate the predicted path.

The predicted path includes one or more actions performed by the interacting individual that change the baseline mental state of the portrayed individual to be more like the target mental state. As will be explained in more detail subsequently, mental state adjuster 100 can simulate the predicted path by generating a plurality of intermediate points, where each intermediate point is generated by adjusting the baseline mental state in one or more dimensions of the multidimensional mental state model according to an amount associated with an action performed by the interacting individual who is interacting with the portrayed individual (i.e., the individual for whom the baseline mental state was generated with baseline mental state prediction module 140). The intermediate point that is closest to the target mental state can be stored as a preferred intermediate point and the action associated with that intermediate point can be stored. The closest point can be determined by, for example, comparing the Euclidean distances between the plurality of intermediate points and the target mental state. The preferred intermediate point can then be used stored used to simulate a new, second plurality of intermediate points to determine a second preferred intermediate point along the predicted path. The intermediate point of the new, second plurality of intermediate points that is closest to the target mental state can also be stored as a second preferred intermediate point along the predicted path and the action associated with that predicted point can be stored.

The simulation process can be iterated until the predicted path includes a point that is within a threshold value of the target mental state. The threshold distance can be based on, for example, a percentage difference between one or more dimension of the multidimensional mental state model and the target mental state. For example, the threshold value can be 10% of a value of the target mental state, such that mental state adjuster 100 stops simulating the predicted path when each value (i.e., the value in each dimension) of the last point along the predicted path is within a range of 90%-110% of each corresponding value of the target mental state. When mental state adjuster 100 reaches the threshold distance, mental state adjuster 100 can output all actions associated with the predicted path to the interacting individual (i.e., the individual interacting with the individual captured in the video data). The interacting individual can then perform the actions to change the mental state of the portrayed individual (i.e., the individual for whom the baseline mental state was generated) toward the target mental state and, in some examples, to a point within the threshold distance of the target mental state. The actions can be output as, for example, one or more instructions for performing the actions.

In operation, mental state adjuster 100 can use programs of baseline mental state prediction module 140 to predict the current, baseline mental state of an individual 112A-N portrayed in video data 110A-N. Mental state adjuster 100 can use programs of target mental state identification module 150 to identify a target mental state for the individual. After the baseline mental state has been predicted and the target mental state has been identified, mental state adjuster 100 can use programs of predicted path simulation module 160 to determine a predicted path from the baseline mental state toward the target mental state. The interacting individual can perform the actions of the predicted path to adjust the mental state of the portrayed individual from the baseline mental state toward the target mental state. Adjustment of the baseline mental state can cause, in turn, improved performance of a task performed by the portrayed individual. In some examples, the interacting individual can use the actions output by mental state adjuster 100 to aid their performance of an instructional task in order to improve the performance of a different task performed by the portrayed individual.

Memory 104 also stores multidimensional mental state model 170, which is a model for classifying the mental state of an individual 112A-N portrayed in video data 110A-N. Multidimensional mental state model 170 includes first dimension 172 and second dimension 174. As used herein, a "multidimensional mental state model" refers to a model of mental state that assigns different aspects of mental state to different dimensions of the model. Advantageously, multidimensional mental state models describe mental state more accurately than existing models of mental state. Because mental state models more accurately describe an individual's mental state, multidimensional mental state models significantly improve the resolution and accuracy of predictions of mental state as compared to existing models, including single-dimensional models of mental state. Multidimensional mental state model 170 includes two dimensions (i.e., first dimension 172 and second dimension 174) in FIG. 1 for explanatory purposes, and can include any number of dimensions. First dimension 172 and second dimension 174 are shown as perpendicular in FIG. 1, but can have non-perpendicular orientations in other examples.

Referring to multidimensional mental state model 170, first dimension 172 can represent an intensity of an individual's mental state and second dimension 174 can represent a pleasantness of the individual's mental state. Different mental states can be described by different combinations of values in first dimension 172 and second dimension 174. For example, each quadrant of multidimensional mental state model 170 can represent a different mental state or different subregions of multidimensional mental state model 170 (including subregions entirely within and/or extending across quadrants of multidimensional mental state model 170) can represent different mental states.

Additionally and/or alternatively, the dimensions of multidimensional mental state model 170 can represent specific aspects of mental state, such as the intensity of the individuals' mental state and/or the pleasantness of the individual's mental state. The dimensions of multidimensional mental state model 400 can also represent mental state by describing aspects of information communicated by the individual (i.e., in the image data, audio data, and/or semantic text data for an individual), such as the relative importance of the information the individual is conveying information, the positivity of the information the individual is conveying, and/or the subject of the conversation in which the individual is participating (e.g., whether the subject is administrative, technical, etc.), among other options.

In other examples, each of first dimension 172 and second dimension 174 can represent separate mental states. For example, first dimension 172 can represent a first mental state, such as confusion, and second dimension 174 can represent a second mental state, such as calmness. Various regions, such as quadrants, of multidimensional mental state model 300 can represent different combinations of confusion and calmness, with each region representing a discrete overall mental state. Simultaneously monitoring confusion and calmness can be used to, for example, measure how well an individual is retaining information as audience members to a presentation or lecture. More specifically, a quadrant with positive confusion and calmness values can represent an overall "confused and attentive" mental state; a quadrant with negative confusion and calmness values can represent an overall "comprehending and attentive" mental state; a quadrant with negative confusion and negative calmness can represent an overall "comprehending and inattentive" mental state; and a quadrant with positive confusion and negative calmness can represent an overall "confused and inattentive" mental state. Other combinations can used to measure other mental overall states and/or performance characteristics.

In other examples, the dimensions of multidimensional mental state model 170 can represent any other combination of mental states. For example, the dimensions of multidimensional mental state model can include one or more of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui.

Points 180-186 represent different combinations of values along the first dimension and the second dimension of multidimensional mental state model 170. In examples where first dimension 172 and second dimension 174 represent intensity and pleasantness of an individual's mental state, respectively, point 180 corresponds to a mental state having relatively high intensity and relatively high pleasantness, such as happiness. Point 182 corresponds to a mental state having relatively high intensity and relatively low pleasantness, such as frustration or annoyance. Point 184 corresponds to a mental state having low intensity and low pleasantness, such as boredom. Point 186 corresponds to a mental state having low intensity and high pleasantness, such as relaxation. In other examples, different combinations of values in first dimension 172 and second dimension 174 can represent different mental states.

As will be explained in further detail subsequently, multidimensional mental state models, such as multidimensional mental state model 170, more accurately describe the mental state of an individual than mental state models having only a single dimension. For example, multidimensional mental state model 170 enables the mental states of amusement, excitement, happiness, delight, gladness and pleasure to be distinguished. Existing, one-dimensional models of mental state are unable to clearly distinguish between closely related mental states. Further, multidimensional mental state models having more than two dimensions more accurately describe the mental state of an individual than mental state models having only two dimensions. For example, it is possible for an individual to be confused, envious, and sleepy simultaneously. A three-dimensional mental state model having dimensions describing each of confusion, envy, and sleepiness can more accurately describe the mental state of an individual experiencing all three mental states to varying degrees than existing representations or models of mental state. As such, the use of a multidimensional mental state model enables significantly more accurate prediction of an individual's mental state.

Baseline mental state prediction module 140 can be used to generate values for each dimension of multidimensional mental state model 170 for an individual. In some examples, baseline mental state prediction module 140 can use different types of data (i.e., image, audio, and semantic text) can be used to generate values for each of first dimension 172 and second dimension 174. The use of different combinations of the three types of information present in video data provides further advantages and improvements to both the efficiency and accuracy of the multidimensional mental state model. More specifically, excluding different combinations of image, audio, and text data allows mental state predictions to be made using only predictive data rather than non-predictive data. For example, text data may offer significantly more insight into the importance of a particular discussion than image or audio data. The multidimensional mental state model can be configured so that only features from the text data are used to calculate the dimension associated with discussion importance, improving accuracy by disregarding non-predictive data and, consequently, improving efficiency by only requiring one type of data to calculate the dimensional value for the discussion importance dimension.

The target mental state identified by target mental state identification module 150 can also be defined by values in first dimension 172 and second dimension 174. The predicted path simulated by predicted path simulation module 160 can also be defined as a series of changes in value in at least one of the first dimension 172 and second dimension 174 and actions corresponding to those changes.

While multidimensional mental state model 170 is depicted in FIG. 1 as only including first dimension 172 and second dimension 174, additional dimensions can be added to multidimensional mental state model 170 as required for a given application and/or operational need. Adding additional dimensions to multidimensional mental state model 170 can allow nearby or similar mental states to be further distinguished, thereby improving the resolution of multidimensional mental state model 170. For example, additional dimensions describing importance of discussed information, the positivity of the information, the subject of the information (e.g., whether the information is administrative, technical, etc.), and/or other mental states can further be used to resolve and distinguish between similar overall mental states.

The dimensions of multidimensional mental state model 170 or any other multidimensional mental state model described herein can be arranged orthogonally, as depicted in FIG. 1, or non-orthogonally. Where multidimensional mental state model 170 includes additional dimensions, the additional dimensions can be arranged orthogonally or non-orthogonally to the other dimensions of multidimensional mental state model 170.

In operation, mental state adjuster 100 allows for the prediction of the baseline mental state based only on information communicated by an individual 112A-N portrayed in video data 110A-N captured by cameras 108A-N. Conventional methods of predicting mental state rely on complex biometric data. Collecting biometric data can require complex machines and, further, often requires physically-intrusive methods. Conversely, mental state adjuster 100 allows for mental state to be predicted using only video data 110A-N, which can be collected using only cameras 108A-N and without the use of any physically-intrusive techniques. Mental state adjuster 100 is then able to determine actions for changing the individual's mental state to be more like the target mental state, and the interacting individual can perform those actions to change their mental state. The change in mental state can, for example, cause a concomitant improvement in performance of a task. As such, mental state adjuster 100 allows for the identification of actions that can be taken to improve task performance based only on video data of an individual.

Figure 2:
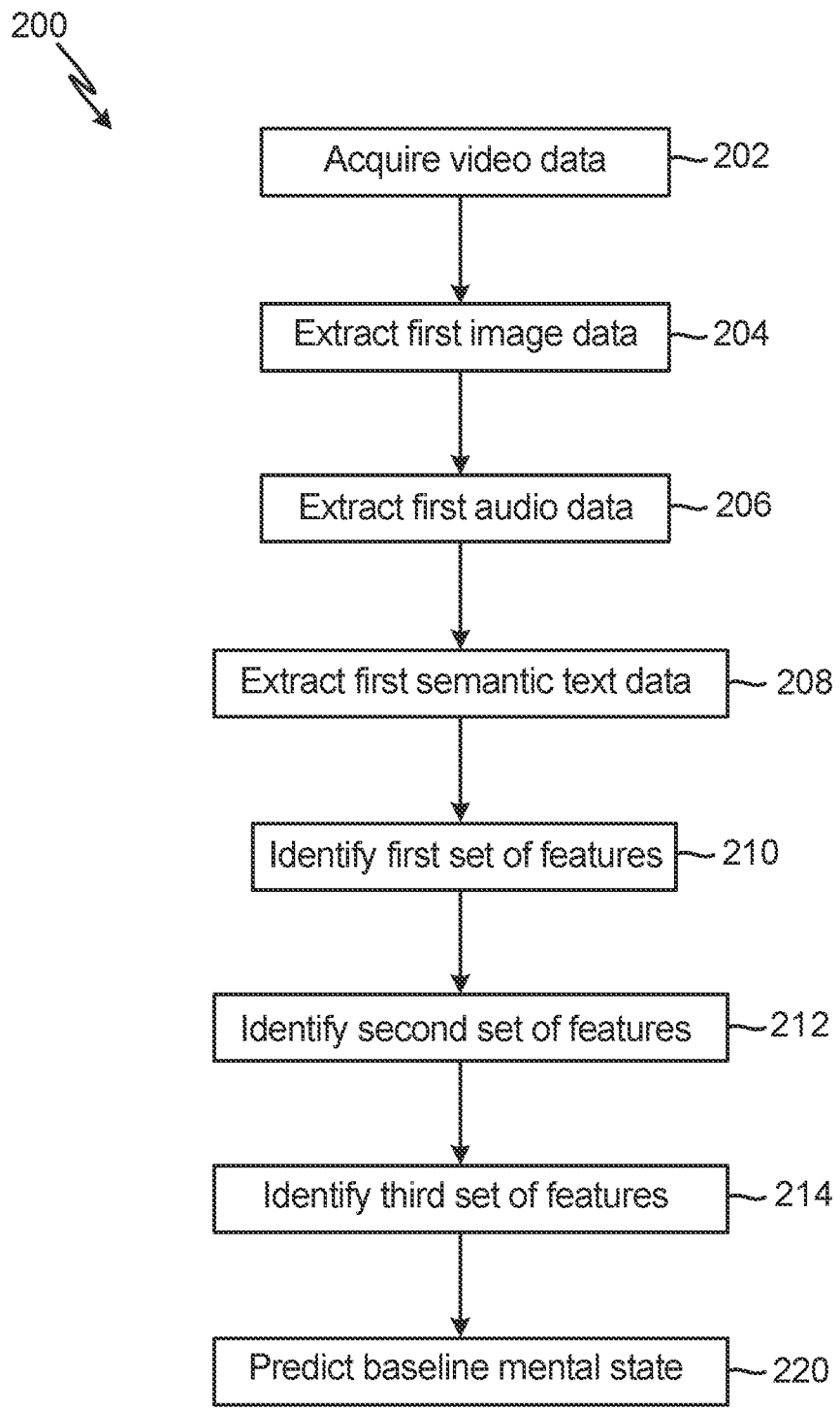
FIG. 2 is a flow diagram of an example of a method of determining a baseline mental state.

FIG. 2 is a flow diagram of method 200, which is a method of predicting a baseline mental state for a portrayed individual. Method 200 includes steps 202-220 of acquiring video data (step 202), extracting image data (step 204), extracting audio data (step 206), extracting semantic text data (step 208), identifying a first set of features (step 210), identifying a second set of features (step 212), identifying a third set of features (step 214), and predicting a baseline mental state (step 220). Method 200 can be performed by mental state adjuster 100 or any other suitable device. Method 200 can be stored to memory 104 of mental state adjuster 100 and executed by processor 102. For explanatory purposes, method 100 is described herein with reference to mental state adjuster 100. Method 200 is performed to determine a baseline mental state for a portrayed individual performing a task and for whom performance improvement is desired. As will be explained in more detail subsequently, method 500 (FIG. 5) allows for automated production of actions that can be performed by an interacting individual to adjust the mental state of the portrayed individual for whom a baseline mental state is predicted using method 200. The mental state adjustment is selected to improve the portrayed individual's task performance.

Method 200 allows for the prediction of a baseline mental state that can be used with other methods described herein (e.g., method 500 described subsequently with respect to FIG. 5). The baseline mental state created by method 200 is a predicted mental state for an individual 112A-N as captured in video data 110A-N. As will be explained in more detail subsequently, method 200 allows for the prediction of the mental state of an individual portrayed in video data based only on the video data and does not require additional data (e.g., biometric data) to predict a mental state.

Steps 202-206 relate to acquiring video data and separating the video data into image, audio, and semantic text components. As referred to herein, "semantic text data"

refers to data that represents spoken words, phrases, sentences, and other sounds produced by an individual as readable text. Steps 202-206 can be performed by, for example, one or more programs of video processing module 120 of mental state adjuster 100 (FIG. 1). In step 202, video data is acquired. The video data can be any media source having both audio and image components. The video data depicts the portrayed individual and generally includes footage of the portrayed individual performing a task. The task can be any task at which the improved performance or competency of the portrayed individual is desired. The video data is not required to depict the interacting individual, but in some examples the video data can depict the interacting individual.

In some examples, the video data also includes semantic text data describing words spoken in the audio component of the video data. The video data can be delivered to mental state adjuster 100 from a video source (e.g., one of cameras 108A-N) and/or mental state adjuster 100 can request the video data from the video source. The video source can be any suitable source of video, such as a multimedia file, a video stream, or one of cameras 108A-N (i.e., one of video data 110A-N). The video data can be of any length, but in some examples, the video data is sampled at pre-determined intervals for use with method 200. Method 200 can be performed for each segment of the video data and updated mental state information can be provided for each segment.

The image data is stored to memory 104 as a series of still images for use with later steps of method 200 and depicts the target portrayed individual. For example, the image data can depict one of individuals 112A-N. The first image data can be extracted by processor 102 of mental state adjuster 100 (FIG. 1) with one or more programs of video processing module 120. Where the video data portrays multiple individuals, the image data extracted from that video data can be cropped to only include the individual for whom baseline mental state information is sought. The individual can be selected by, for example, input at user interface 106 or by another suitable method. Processor 102 can identify an individual from the still image data and crop each image of the still image data to include only that individual. The still image data can include one image for each frame of the video data or can be sampled at a pre-determined rate. For example, the video data can be sampled once every three frames to generate the still image data.

In some examples, the still image data derived from the video data may contain images in which the individual of interest is not present. In these examples, the image data can be trimmed to include only images in which the individual is present. The trimmed, cropped image data can then be stored to memory 104 as the image data.

In step 206, audio data is extracted from the video data. The extracted audio data is stored to memory 104 for use with later steps of method 200 and includes audio of the individual depicted in the image data. The audio data can be extracted by processor 102 of mental state adjuster 100 (FIG. 1) with one or more programs of video processing module 120. Where the video data that portrays the individual also includes other individuals, the audio data extracted from that video data can be trimmed to include audio of only one individual. The trimmed audio can be stored to memory 104 as the extracted audio data. The audio can be trimmed by, for example, diarizing the audio file to separate the audio extracted from the video data for each individual captured in the audio data.

In some examples, processor 102 can execute one or more programs stored on memory 104 to identify which portions of the audio data in which an individual is communicating and trim the audio data to include only those portions. Trimming the audio data can reduce the file size of the audio data, which can improve the case with which steps 212 and/or 220 can be performed in some examples. The program can be, for example, a computer-implemented machine learning model trained to identify individuals based on voices present in audio data.

Where the video data includes multiple individuals, processor 102 of mental state adjuster 100 (FIG. 1) can use one or more programs stored to memory 104 to determine which portions of the audio correspond to the include the portrayed individual for whom baseline mental state information is sought (i.e., the individual portrayed in the image data extracted in step 204). For example, processor 102 can execute one or more programs to identify individuals present in the image data and individuals present in the audio data. The processor 102 can cross-reference a library of individuals to determine which diarized or trimmed audio files correspond to the individual in the image data extracted in step 204 and store those audio files as the extracted audio data in step 206. Additionally and/or alternatively, the processor 102 can execute one or more programs to analyze the image data and determine when the portrayed individual is talking. The processor 102 can then use that timestamp information to determine which portions of the untrimmed audio correspond to the individual portrayed in the image data and store those portions of the audio as the extracted audio data in step 206.

In step 208, the semantic text data is extracted. The semantic text data can be, for example, a transcript of the words spoken in the audio portion of the video data. The semantic text data can be extracted from, for example, the audio data extracted in step 206. Processor 102 of mental state adjuster 100 (FIG. 1) can use one or more programs of video processing module 120 to extract the semantic text data. The semantic text data can be extracted from the audio data using a text-to-speech program or another suitable tool and can be stored as the extracted semantic text data in step 208. In other examples, the video data can include a semantic text transcript of words, phrases, sentences, etc. spoken by the portrayed individual, and the semantic text data can be extracted directly from the video data.

In step 210, the image data extracted in step 206 is analyzed to generate a first feature set. The features can be identified using a computer-implemented machine learning model trained to identify features from the image data extracted in step 204. Step 210 can be performed by programs and/or machine learning models of feature extraction module 130. The programs and/or machine learning models can include, for example, one or more computer vision models. The features identified in step 206 are features related to information conveyance, such as body language visible in the image data. In some examples, the machine learning model can be trained only to identify features related to task performance. In other examples, a first machine learning model can be trained to identify a broad set of features visible in the image data, including features that are not related to task performance, and features related to task performance can be determined by a second computer-implemented machine learning model for use with subsequent steps of method 200. The features can include one or more of, for example, hand gestures, head tilt, the presence and amount of eye contact, the amount of eye blinking, forehead wrinkling, mouth position, mouth shape, eyebrow shape, eyebrow position, or another body language element indicative of information conveyance and/or mental state.

In step 212, the audio data extracted in step 206 is analyzed to generate a second feature set. The features can be identified using a computer-implemented machine learning model trained to identify features from the audio data. Step 212 can be performed by programs and/or machine learning models of feature extraction module 130. The features identified in step 212 are features related to information conveyance, such as vocal tone or cadence. In some examples, the machine learning model can be trained only to identify features related to task performance. In other examples, a first machine learning model can be trained to identify a broad set of features present in the audio data, including features that are not related to task performance, and features related to task performance can be determined by a second computer-implemented machine learning model for use with subsequent steps of method 200. The features can include, for example, pitch, intonation, inflection, sentences stress, or another audio element indicative of information conveyance and/or mental state.

In some examples, the audio data can be converted to an audio spectrogram and that can be analyzed in step 212 to generate the second feature set. The spectrogram can describe, for example, the amplitude or frequency ranges of the audio data. In some examples, processing the audio data as an audio spectrogram enables processor 102 to more easily identify features in the audio data.

In step 214, the semantic text data extracted in step 208 is analyzed to generate a third feature set. The features can be identified using a computer-implemented machine learning model trained to identify features from the semantic text data. The features can be, for example, phonemes, words, phrases, sentences, or other units of language that convey information and are stored in the semantic text data. The features can also be, for example, one or more intents and/or one or more entities in the semantic text data, as recognized by a natural language understanding model. A classifiable intent can include, for example, the intended meaning of a semantic text phrase. A classifiable entity can include, for example, words, phrases, sentences, or other units of language that provide additional context to further describe or classify an intent. Step 226 can be performed by programs and/or machine learning models of feature extraction module 130.

In step 220, a baseline mental state is predicted for the individual portrayed in the video data. As described previously, the baseline mental state is predicted based on data derived from the video data acquired in step 202 and predicts the mental state of an individual portrayed in the video data. The baseline mental state can be used by other methods described herein to determine a predicted path to a target mental state. The baseline mental state predicted in step 220 can optionally be output to the portrayed individual so that the portrayed individual is aware of their own baseline mental state before that baseline mental state is adjusted. Additionally and/or alternatively, the baseline mental state predicted in step 220 can be optionally output to the interacting individual so that the interacting individual is aware of the portrayed individual's baseline mental state before adjusting that baseline mental state.

Mental state adjuster 100 makes a prediction of the portrayed individual's baseline mental state based on features of one or more of the first feature set, the second feature set, and the third feature set generated in steps 210, 212, and 214, respectively. In some examples, the baseline mental state can be predicted using a multidimensional mental state model, such as multidimensional mental state model 170 discussed with respect to FIG. 1. The feature sets of the first, second, and third feature sets used to generate the baseline mental state can be selected based on their predictive power for predicting mental state. For example, features of certain ones of the first, second, and third feature sets may have strong predictive power for one dimension of a multidimensional mental state model used to predict the baseline mental state and weak predictive power for another dimension of the multidimensional mental state model. Additionally and/or alternatively, the task or activity used to identify a target mental state can be used to select the feature sets of the first, second, and third feature sets that are used to generate the baseline mental state.

Advantageously, method 200 allows prediction of mental state based solely on video data of an individual rather than on biometric measurements or other more invasive measurement techniques. Further, as method 200 uses a multidimensional mental state model, the method 200 provides numerous advantages over existing models of mental state. Particularly, the multidimensional mental state models used by method 200 are scalable and can include any number of dimensions based on operational need. The dimensions can advantageously include any combination of mental states and mental state components, including factors that contribute to mental state and aspects of communicated information.

As method 200 is configured to predict mental state using a multidimensional mental state model, the predictions of mental state made using method 200 are substantially more accurate than predictions made using existing methods. The improved mental state prediction accuracy enabled by method 200 significantly increases the accuracy of the predicted path generated using method 500, as discussed in more detail subsequently with respect to FIG. 5.

Figure 3:
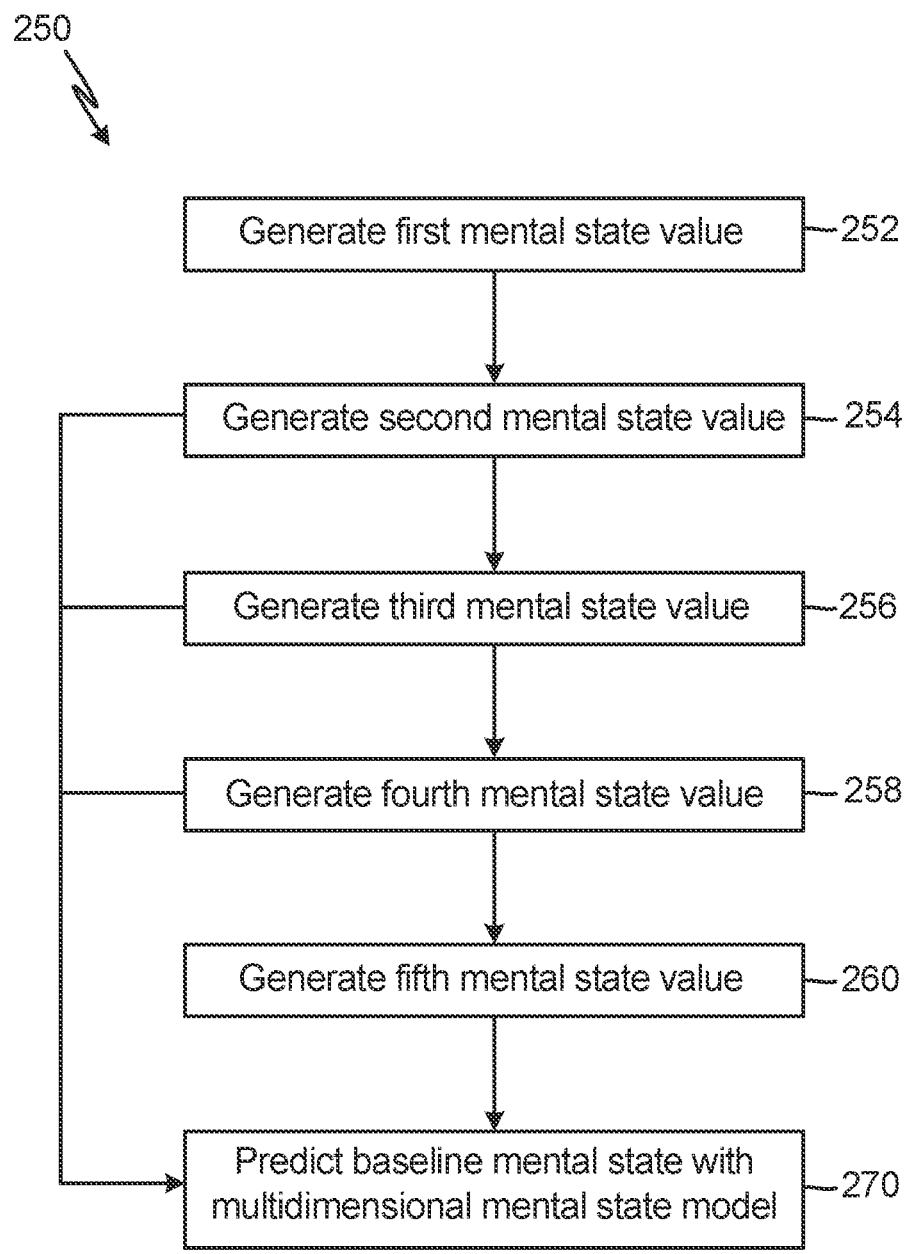
FIG. 3 is a flow diagram of an example of a method of generating values for predicting mental state with a multidimensional mental state model suitable for use with the method of FIG. 2.

FIG. 3 depicts method 250, which is a method for generating values for predicting mental state with a multidimensional mental state model during step 220 of method 200 (FIG. 2). Method 250 includes steps 252-270 of generating a first mental state value (step 252), generating a second mental state value (step 254), generating a third mental state value (step 256), generating a fourth mental state value (step 258), generating a fifth mental state value (step 260), and predicting a baseline mental state with a multidimensional mental state model (step 270).

Method 250 allows for prediction of a baseline mental state by generating values for each dimension of the multidimensional mental state model based on the first, second, and/or third feature sets extracted in steps 210, 212, and 214 of method 200 (FIG. 2), respectively. Processor 102 can perform method 250 using one or more programs of baseline mental state prediction module 140. In some examples, processor 102 can use one or more computer-implemented machine learning models trained to predict values for one or more dimensions based on features of the first, second, and/or third feature sets.

Each dimension of the multidimensional mental state model used in method 250 can correspond to one or more mental states or components of mental state. Each dimension can describe, for example, a mental state, such as tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui. Additionally and/or alternatively, each dimension can describe a component of a mental state, such as the intensity of a mental state, the pleasantness of the mental state, the importance of information communicated by the individual, the positivity of the information communicated by the individual, or the subject of the information (e.g., whether the information is administrative, technical, etc.), among other options.

In step 252, a first mental state value is generated. Processor 102 can use one or more programs of baseline mental state prediction module 140 and features of one or more of the first, second, and third feature sets identified in steps 210-214 to generate the first mental state value. The first mental state value describes a value in a first dimension of the multidimensional mental state model. The features used to generate the first mental state value can be selected based on their predictive power to generate the second mental state value. For example, only the third feature set identified in step 214 of method 200 (i.e., the feature set corresponding to the semantic text data) may have predictive power in examples where the first dimension of the multidimensional mental state model is the importance of discussed information. In other examples, the first and/or second feature sets may have predictive power and the third feature set may lack predictive power.

The first mental state value can be a numeric representation of, for example, an intensity of the first mental state. Additionally and/or alternatively, the first mental state value can represent a number of features associated with the second mental state that are present in the first set of features. In further examples, the first mental state value can be a score representing a likelihood that the individual is experiencing a first mental state.

In step 254, a second mental state value is generated. The second mental state value generated in step 254 is generated in substantially the same way as the first mental state value generated in step 252. However, the second mental state value describes a value in a second dimension of the multidimensional mental state model rather than a value in the first dimension of the multidimensional mental state model. Further, the features sets used to generate the second mental state value do not have to be the same feature sets used to generate the first mental state value, but may be in some examples. The feature sets used to generate the second mental state value can also be selected based on their predictive power to generate the second mental state value.

Similar to the first mental value, the second mental state value can be a numeric representation of, for example, an intensity of the second mental state. Additionally and/or alternatively, the first mental state value can represent a number of features associated with the second mental state that are present in the first set of features. In further examples, the second mental state value can be a score representing a likelihood that the individual is experiencing a second mental state.

Steps 256-260 are optional performed in substantially the same way as described previously with respect to steps 252 and 254. Steps 256, 258, and 260 are only performed if the multidimensional mental state model used to predict the baseline mental state includes third, fourth, and fifth dimensions, respectively. Where the multidimensional mental state model lacks third, fourth, and fifth dimensions, method 250 can proceed to step 270 after step 254. Similarly, where the multidimensional mental state model lacks fourth and fifth dimensions, method 250 can proceed to step 270 after step 256. Where the multidimensional mental state model lacks only the fifth dimension, method 250 can proceed to step 270 after step 258.

In step 270, the portrayed individual's baseline mental state is predicted. The portrayed individual's baseline mental state is the position in the multidimensional mental state model that corresponds to the values produced in steps 252, 254, and those of optional steps 256-260 that were performed. In some examples, the multidimensional mental state model can be divided into regions that correspond to specific mental states. Using multidimensional mental state model 170 as an example, each quadrant of multidimensional mental state model 170 can represent a different mental state. Additionally and/or alternatively, different subregions of multidimensional mental state model 170 can represent different mental states, including subregions entirely within and/or extending across quadrants of multidimensional mental state model 170.

The use of a multidimensional mental state model significantly increases the granularity and accuracy of mental state predictions as compared to existing methods. Many existing methods of analyzing mental state attempt to identify mental state based only on the presence or absence of features associated with a particular mental state. Where a model is used to analyze mental state, existing methods use a model that contains at most a single dimension, with different mental states ordered along the single dimension of mental state. Advantageously, the use of a multidimensional mental state model allows for significant improvements in resolution between similar overall mental states, which significantly improves the accuracy of mental state predictions made using the multidimensional mental state model.

Figure 4:
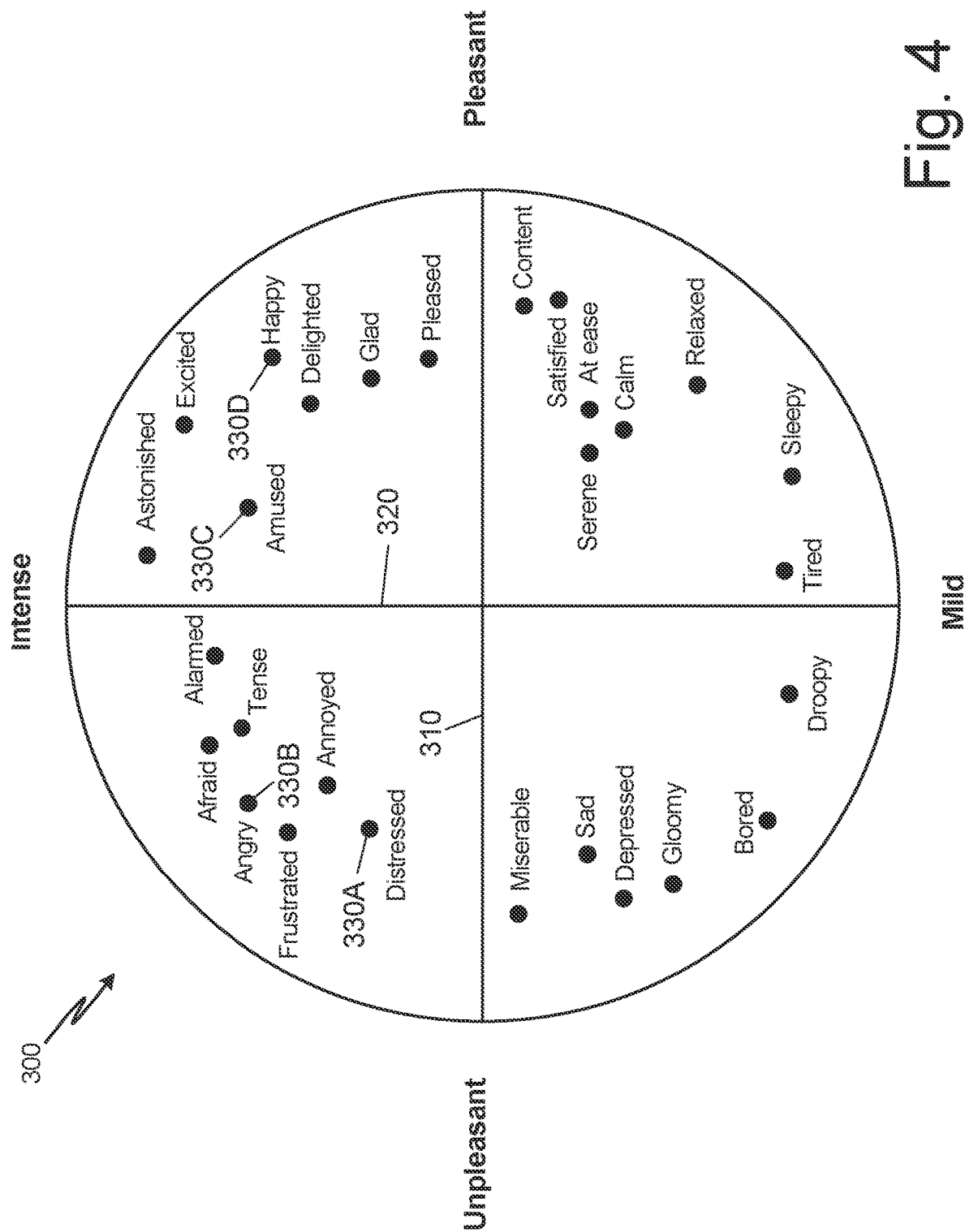
FIG. 4 is a schematic diagram of an example of a multidimensional mental state model.

FIG. 4 is a schematic diagram of multidimensional mental state model 300, which is an example of a multidimensional mental state model suitable for use with methods 200 (FIG. 2) and 250 (FIG. 3). Multidimensional mental state model 300 is only one example of a multidimensional mental state model but includes annotations for specific mental states that illustrate the advantages of predictions made using multidimensional mental state models as compared to existing methods.

Multidimensional mental state model 300 is a two-dimensional mental state model and includes first dimension 310, second dimension 320, first mental state 330A, second mental state 330B, third mental state 330C, and fourth mental state 330D. In the depicted example, first dimension 310 describes the pleasantness of the portrayed individual's mental state. A low or negative value along first dimension 310 corresponds to an unpleasant mental state, while a high or positive value along first dimension 310 corresponds to a pleasant mental state. Second dimension 320 describes the intensity of the portrayed individual's mental state. A low or negative value along second dimension 320 corresponds to a mild or non-intense mental state, while a high or positive value along second dimension 320 corresponds to an intense mental state. Like multidimensional mental state model 170, the multidimensional mental state model 300 is depicted as having perpendicular dimensions, but can have dimensions in other orientations in other examples.

According to multidimensional mental state model 300, different mental states can be assigned various values relating to pleasantness and intensity of the mental state. For example, the portrayed individual's mental state can be both intense and unpleasant (e.g., afraid), mild and unpleasant (e.g., bored), pleasant and mild (e.g., relaxed), and/or intense and pleasant (e.g., happy).

By including multiple dimensions, multidimensional mental state model 300 can distinguish between mental states that have similar intensities but are dissimilarly pleasant, and between mental states that are similarly pleasant but that have different intensities. For example, multidimensional mental state model can distinguish between, for example, excitement and satisfaction, between alarm and astonishment, between distress and sadness, and between boredom and relaxation.

Further, multidimensional mental state model 300 can more clearly distinguish between mental states having generally similar pleasantness and intensities as compared to existing methods using a single dimension to distinguish between different mental states. For example, points 330A and 330B, which correspond to "distressed" and "angry" mental states, respectively, are difficult to resolve by pleasantness alone due to their similar pleasantness values. However, points 330A and 330B can be resolved by their intensity values, which are more dissimilar than the pleasantness values for points 330A and 330B. Similarly, points 330C and 330D, which correspond to "happy" and "amused" mental states, respectively, are difficult to resolve based on their intensity values. However, points 330C and 330D can also be resolved according to their pleasantness values, which are more dissimilar than their intensity values. These examples highlight the manner in which multidimensional mental state model 300 provides improved granularity and resolution of mental state as compared to existing models. As multidimensional mental state model 300 is able to more clearly distinguish between mental states having similar values along one dimension, multidimensional mental state model 300 is also able to represent a more complex set of mental states than existing mental state models using a single-dimension. Further, the inclusion of multiple dimensions significantly improves the resolution of multidimensional mental state model 300 by more clearly differentiating between different mental states than existing models. The improved resolution of multidimensional mental state model 300 allows for significantly more accurate predictions of mental state than existing models.

Notably, adding additional dimensions to multidimensional mental state model 300 can allow nearby or similar mental states to be further distinguished. For example, additional dimensions describing information importance, information positivity, and/or the subject of the information (i.e., whether the information is administrative, technical, etc.) can further be used to resolve and distinguish between similar overall mental states. In examples where each dimension of the multidimensional mental state model represents a separate mental state (e.g., one or more of confusion, envy, calmness, sleepiness, etc.), the inclusion of additional dimensions can also allow for more accurate description of an individual's mental state.

In examples where each dimension of the multidimensional mental state model represents a separate mental state (e.g., one or more of confusion, envy, calmness, sleepiness, etc.), adding additional mental state can also allow for more accurate description of an individual's mental state. For example, a three-dimensional mental state model can describe three separate mental states that an individual may be experiencing simultaneously and that contribute to the individual's overall mental state. Similarly, a four-dimensional mental state model can describe four separate mental states and a five-dimensional mental state model can describe five separate mental states. Other examples of mental state models with more than five dimensions are contemplated herein.

Additional dimensions can be added to the multidimensional mental state model as required for a given application. As each dimension can be determined with different weights assigned to and/or with different combinations of image, audio, and semantic text data, as described previously, increasing the number of dimensions of the multidimensional mental state model also increases the number of distinct mental states described by the multidimensional mental state model, improving the resolution of the model and allowing for more accurate mental state predictions.

FIG. 5 is a flow diagram of method 500, which is a method of determining actions for adjusting mental state. Method 500 includes steps 504-508 of identifying a target mental state (step 504), simulating a predicted path toward the target mental state from the baseline mental state (step 506), and outputting actions for adjusting mental state according to the predicted path (step 508). Method 500 is performed in combination with method 200 (FIG. 2) and the actions determined using method 500 are actions that can be performed by the interacting individual to adjust the mental state of the portrayed individual (i.e., an individual for whom a baseline mental state was generated using method 200). Step 504 can be performed substantially simultaneously as method 200, prior to performance of method 200, or following the prediction of the baseline mental state in step 220 of method 200. Step 506 is performed following both step 504 and step 220 of method 200. Step 508 is performed following step 506.

In step 504, a target mental state is identified. The target mental state is a point in the multidimensional mental state model that is associated with effective performance of a task or activity. The target mental state can be identified according to a task or activity performable by the portrayed individual for whom the baseline mental state was determined in step 220 of method 200 (FIG. 2). Processor 102 can use one or more programs of target mental state identification module 150 (FIG. 1) to identify the target mental state. The one or more programs can be, for example, one or more machine learning programs configured to identify the task or activity the portrayed individual is performing from the image, audio, and/or semantic text data extracted in steps 204, 206, and 208, respectively, of method 200. Additionally and/or alternatively, the task or activity can be determined based on user input, such as input at user interface 106 (FIG. 1).

Once the task or activity the portrayed individual is performing is identified, the task or activity can be used to identify the target mental state for the portrayed individual. The target mental state can be identified by, for example, cross-referencing the task or activity with a table that correlates tasks and activities with target mental states. Additionally and/or alternatively, a computer-implemented machine learning model trained to relate performable activities and/or tasks to target mental state can be used to determine the target mental state. The computer-implemented machine learning model can also be trained to relate additional factors to target mental state. For example, the computer-implemented machine learning model can be trained to relate other characteristics of the portrayed individual (e.g., age, grade-level, etc.) in addition to the selected activity and/or task to target mental state.

The target mental state includes at least one dimension of mental state in common with the baseline mental state, but does not necessarily include identical dimensions or an identical number of dimensions. Where the baseline mental state and target mental state do not have identical dimensions, only the dimensions of the baseline mental state and target mental state are used to simulate the predicted path in subsequent step 506. For example, the baseline mental state predicted in step 220 (method 200; FIG. 2) can be predicted using a three-dimensional model of mental state such that the baseline mental state has three dimensions, while the target mental state identified in step 504 of method 500 can include data for only two dimensions of the three-dimensional mental state model. In this example, the predicted path would be simulated in only the two dimensions shared by the baseline mental state and the target mental state.

In step 506, a predicted path toward the target mental state from the baseline mental state is simulated. The predicted path comprises one or more steps from the baseline mental state predicted in step 220 of method 200, where each step includes one performable action and a corresponding change in mental state. The actions are performable by the interacting individual and can be specific to a task or activity that the interacting individual is performing. Each action can correspond to a change in one or multiple dimensions of mental state according to the multidimensional mental state model used to determine mental state. As described previously, the predicted path is simulated only for the dimensions shared by the baseline mental state and the target mental state. Accordingly, the steps of the predicted path only relate to changes in the shared dimensions of the baseline mental state and the target mental state.

The predicted path is simulated by a simulator using a computer-implemented machine learning model trained to correlate performable actions with changes in mental state. The computer-implemented machine learning model can be trained on a sufficiently large data set of mental states of various portrayed individuals before and after a catalog of actions are performed by one or more interacting individuals, where the actions are performed by interacting with the portrayed individuals. In some examples, the data set of mental states can be specific to portrayed individuals engaged in a particular task. Similarly, the catalog of actions can be specific to a task performed by the interacting individual. For example, if the task performed by the interacting individual is teaching or lecturing, the catalog of actions can be selected to be tasks associated with teaching or lecturing. As such, whether a particular action results in a change in value to one or multiple dimensions of mental state is based on the training data used to train the computer-implemented machine learning model. In these examples, a plurality of computer-implemented machine learning models can be trained for a plurality of tasks and activities, and the computer-implemented machine learning model used in step 506 can be selected according to the task or activity used to identify the target mental state in step 504. The simulator used to simulate the predicted path can be any suitable software program or combination of software programs for simulating changes to mental state based on inputs from the computer-implemented machine learning model.

The simulator simulates the predicted path in steps with each step corresponding to single actions and changes in mental state. The simulator simulates the first step of the predicted path by simulating a plurality of intermediate points using the baseline mental state, the trained computer-implemented machine learning model, and the plurality of actions. Each intermediate point corresponds to the mental state predicted to result from an interacting person performing one of the actions to a person having the baseline mental state. The intermediate point with the shortest Euclidean distance to the target mental state is selected as a preferred intermediate point, indicating that it is preferred over the other intermediate points as a step along the predicted path. The shortest Euclidean distance refers to the Euclidean distance having the lowest value. The Euclidean distance is measured in the space defined by the multidimensional mental state model.

After the first preferred intermediate point is determined, the simulator then simulates the next step along the predicted path by simulating a second plurality of intermediate points using the trained computer-implemented machine learning model, the plurality of actions, and the preferred intermediate point. Each intermediate point of the second plurality of intermediate points corresponds to the mental state predicted to result from a person having the mental state described by the preferred intermediate point. The intermediate point of the second plurality of intermediate points having the shortest Euclidian distance to the target mental state is selected as a second preferred intermediate point, indicating that it is preferred over the other points of the second plurality of intermediate points as a second step along the predicted path. The Euclidean distance is measured in the space defined by the multidimensional mental state model.

The simulator continues to simulate steps along the predicted path until one of the preferred intermediate points is within a threshold distance of the target mental state. In some examples, the most recent preferred intermediate must have identical values in one or more dimensions of the multidimensional mental state model as the target mental state to stop simulating. The threshold distance can be, for example, a Euclidean distance. Additionally and/or alternatively, the threshold distance can be a value representing a maximum acceptable difference between the most recent preferred intermediate point and the target mental state in one of the dimensions of the multidimensional mental state model. The threshold distance is selected such that any point within the threshold distance of the target mental state sufficiently resembles the target mental state to improve task performance. The threshold distance can be user-selected or can be automatically recalled for use during step 506 of method 500.

Figure 6:
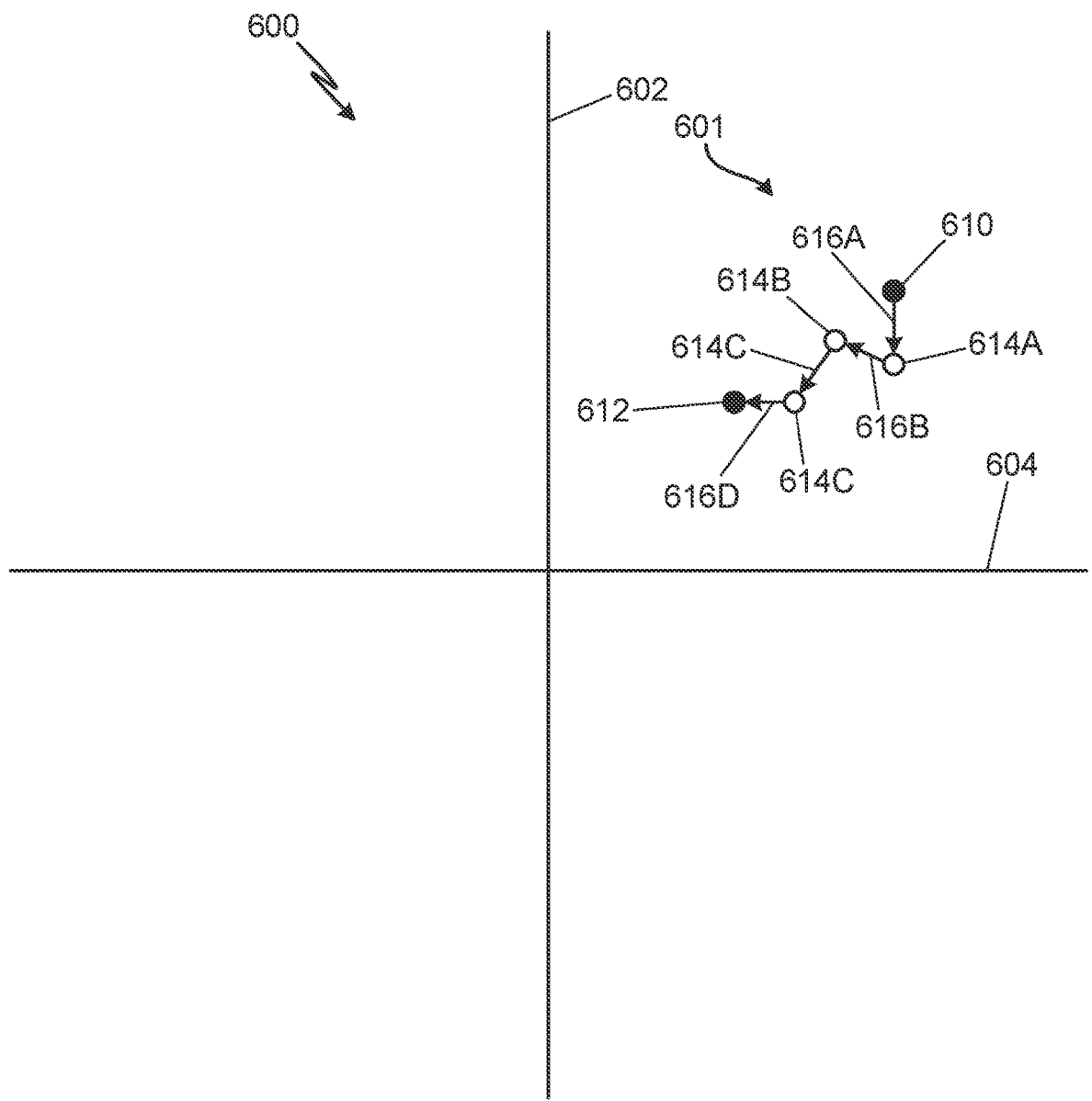
FIG. 6 is schematic diagram of a multidimensional mental state model and includes a schematic representation of a predicted path generated using the method of FIG. 5.

FIG. 6 is a schematic diagram of multidimensional mental state model 600 that includes a schematic representation of predicted path 601. Multidimensional mental state model 600 includes first dimension 602 and second dimension 604. Predicted path 601 includes baseline mental state 610, target mental state 612, preferred intermediate points 614A-C, and action vectors 616A-D. Predicted path 601 is one example of a predicted path where the final preferred intermediate point has the same multidimensional coordinate values as the target mental state, and for clarity, the final preferred intermediate point is omitted from FIG. 6.

Like the dimensions of other multidimensional mental state models described herein, first dimension 602 and second dimension 604 can represent specific aspects of mental state, such as factors that contribute to mental state, and aspects of information communicated by the portrayed individual (e.g., in the image data, audio data, and/or semantic text data for a portrayed individual), the intensity of the individual's mental state, the pleasantness of the individual's mental state, the importance of the information the individual is conveying, the positivity of the information the individual is conveying, and/or the subject of the conversation in which the individual is participating (e.g., whether the subject is administrative, technical, etc.), among other options.

In other examples, the first dimensional 602 and/or second dimension 604 of multidimensional mental state model 600 can represent any other combination of mental states. For example, the dimensions of multidimensional mental state model can also include one or more of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui. As a specific example, the multidimensional mental state model 170 can include three dimensions, where each dimension represents an intensity of a specific mental state. The three dimensions can represent intensities of, for example, frustration, fear, and excitement, respectively.

Baseline mental state 610 is a baseline mental state for a portrayed individual and is predicted according to method 200 (FIG. 2). Target mental state 612 is a target mental state identified in step 504 of method 500 (FIG. 5). Baseline mental state 610 and target mental state 612 are plotted in the depiction of multidimensional mental state model 600 according to their values in first dimension 602 and second dimension 604. Preferred intermediate points 614A-C are preferred intermediate points determined as explained previously with respect to step 506 of method 500. Preferred intermediate points are also plotted in the depiction of multidimensional mental state model 600 according to their values in first dimension 602 and second dimension 604. Each of preferred intermediate points 614A-C represents a step along predicted path 601 with which an action is associated.

Action vectors 616A-D represent the actions and the accompanying changes to mental state used to create the preferred intermediate points 614A-C of predicted path 601. More specifically, each of action vectors 616A-D represents the magnitude and direction of the change in mental state associated with the action used to simulate the steps of predicted path 601 in step 506 of method 500 (FIG. 5) and thereby generate preferred intermediate points 614A-C. Each of action vectors 616A-D is associated with one action performable by an interacting individual through interaction with the portrayed individual having baseline mental state 610.

Action vector 616A represents a change in mental state associated with a first action, and accordingly represents the difference in value between baseline mental state 610 and first preferred intermediate point 614A. Action vector 616B represents a change in mental state associate with a second action, and accordingly represents the difference in value between first preferred intermediate point 614A and second preferred intermediate point 614B. Action vector 616C represents a change in mental state associate with a third action, and accordingly represents the difference in value between second preferred intermediate point 614B and third preferred intermediate point 614C. Action vector 616D represents a change in mental state associate with a fourth action, and accordingly represents the difference in value between third preferred intermediate point 614C and a fourth preferred intermediate point. As the fourth preferred intermediate point has the same values in first dimension 602 and second dimension 604, action vector 616D also represents the difference in value between the third preferred intermediate point 614C and target mental state 612.

As such, adding action vectors 616A-D creates one vector that extends from baseline mental state 610 to the final intermediate point, which in this example has the same values in multidimensional mental state model 600 as target mental state 612. An interacting individual who is interacting with the portrayed individual can perform the actions represented by action vectors 616A-D to adjust the mental state of the portrayed individual from baseline mental state 610 to target mental state 612.

The final intermediate point of predicted path 601 is not required to have the same values in multidimensional mental state model 600 as target mental state 612. The final intermediate point in the example of predicted path 601 depicted in FIG. 6 has the same values as target mental state 612 for explanatory purposes. In other examples, it is possible for the final intermediate point of predicted path 601 to have values that differ from target mental state 612 in one or more dimensions of multidimensional mental state model 600. However, the final intermediate point of predicted path 601 should be within the threshold distance(s) of target mental state 612. In examples where the final intermediate point does not have the same values as target mental state 612, an interacting individual can perform the actions represented by action vectors 616A-D to adjust the mental state of the portrayed individual to the final intermediate point.

The plotted depictions of baseline mental state 610, target mental state 612, preferred intermediate points 614A-C, and action vectors 616A-D are included for explanatory purposes. Plotting is not required to generate a predicted path during step 506 of method 500 (FIG. 5) and, as such, is also not required to plot any of the baseline mental state, the target mental state, any or all preferred intermediate points, and any or all action vectors. However, in some examples, one or more elements of predicted path 601 can be plotted and displayed via a user interface device, such as user interface 106 to visually represent the mental state adjustment predicted using method 500 (FIG. 5) to the portrayed individual for which the baseline mental state was predicted using method 200 (FIG. 2).

As described previously, each action of a predicted path simulated according to method 500 (FIG. 5) can result in changes in one or multiple dimensions of a multidimensional mental state model. In the depicted example, action vectors 616A and 614D represent changes in only first dimension 602 and second dimension 604, respectively. Conversely, action vectors 616B and 614C represent changes in both first dimension 602 and second dimension 604. Other combinations of changes in value in the dimensions of the multidimensional mental state model are possible based on the actions of the plurality of actions used to simulate the predicted path.

While multidimensional mental state model 600 and predicted path 601 are depicted in only two dimensions (i.e., first dimension 602 and second dimension 604), in other examples, multidimensional mental state model 600 can include three or more dimensions. In some of these examples, predicted path 601 can include changes in more than two dimensions. As described previously, in some examples, it may be advantageous for predicted path 601 to include changes in fewer than all dimensions of multidimensional mental state model 600. In other examples, it may be advantageous for predicted path 601 to include changes in all dimensions of multidimensional mental state model 600.

Returning to method 500, the actions corresponding to the predicted path simulated in step 506 are output in step 508. After the predicted path includes a preferred intermediate point within the threshold distance of the target mental state, the simulator stops simulating steps of the predicted path and step 508 is performed. Indications of the actions corresponding to the steps of the predicted path can be output via a user interface device, such as user interface 106. An indication of the actions can include, for example, text, image data, audio, or another suitable means of conveying the actions. The actions are output to the interacting individual (i.e., the individual interacting with the portrayed individual), so that the interacting individual can perform the actions output in step 508.

Performing the actions output in step 508 allows the interacting individual to adjust the mental state of the portrayed individual to improve the portrayed individual's performance of a task or activity. As described previously, the target mental state identified in step 504 corresponds to an ideal or preferred mental state for performing a task or activity. Simulating the predicted path in step 506 provides a list of actions that an interacting individual can perform to adjusting adjust the baseline mental state of the portrayed individual to be more like or the same as the target mental state. The interacting individual can then perform those actions to adjust the portrayed individual's mental state to improve the portrayed individual's task performance. Advantageously, combining methods 200 (FIG. 2) and 500 (FIG. 5) allows for the predicted path to be determined based only on video data of the portrayed individual for whom mental state adjustment and associated task performance improvement is desired and does not require other, more invasive techniques to determine the baseline mental state used in method 500.

In some examples, the actions of the predicted path are cross-referenced with a table that relates actions and instructions for performing those actions for step 508. The instructions for performing the actions can then be output to the interacting individual and performed to adjust their mental state according to the predicted path. Advantageously, outputting instructions for performing actions can improve clarity and usability for the interacting individual by removing guesswork associated with determining how to perform actions with which the interacting individual is unfamiliar or inexperienced. For example, while the interacting individual is usually experienced with the task performed by the portrayed individual for which improvement is desired, the interacting individual may not be experienced with the tasks or actions required to effectively coach, teach, and/or tutor the portrayed individual.

Advantageously, method 500 improves the ability of an individual in a coaching-type role to help another individual improve their performance at a particular task. Method 500 also enables improvement for tasks where instructions to emulate skilled individuals are unlikely to lead to improved task performance. For example, the ability of a student to learn new material is unlikely to be improved by providing instructions or actions for the student to copy the physical behaviors and/or mannerisms of a high-performing student. Similarly, method 500 allows for the automated generation of actions for an interacting individual to adjust the mental state of a portrayed individual and thereby improve that portrayed individual's task performance. The automated generation of actions that lead to performance improvement of another person reduces the relative level of skill or experience at coaching, teaching, and/or tutoring help another individual improve their task performance. Returning to the example of a teacher and a student, method 500 allows for the automated generation of actions that can be performed by the teacher to adjust the student's mental state, thereby improving their performance. As described previously, the actions generated using 500 are often more complex than simple instructions from the teacher to emulate a high-performing student. In these examples, method 500 reduces the relative level of skill or experience required to adequately perform teaching tasks that improve student performance. Further, method 500 can improve the ability of both skilled and unskilled teachers to recognize student mental state and take actions to adjust that mental state to improve performance.

The previous examples refer to teacher-student interactions for illustrative purposes. Notably, as method 200 is able to generate a baseline mental state using non-invasive, video-based techniques, methods 200 and 500 can be advantageously adapted to a wide variety of coaching-type tasks and situations, giving methods 200 and 500 significantly increased flexibility as compared to existing techniques. As another specific example, methods 200 and 500 can be applied to the lecturer-audience relationship with similar or substantially the same benefits as outlined above.

Further, the use of computer-implemented machine learning models allows methods 200 and/or 500 to be performed in real-time or substantially real time, enabling an interacting individual to more quickly act on the actions output by method 500 to adjust the mental state of the portrayed individual to improve task performance of the portrayed individual. In some examples, performing methods 200 and/or 500 in real-time or substantially real-time allows an interacting individual to adjust the mental state of the portrayed individual during the same performance of the task or activity during which a baseline mental state is predicted for the portrayed individual using method 200.

Figure 7:
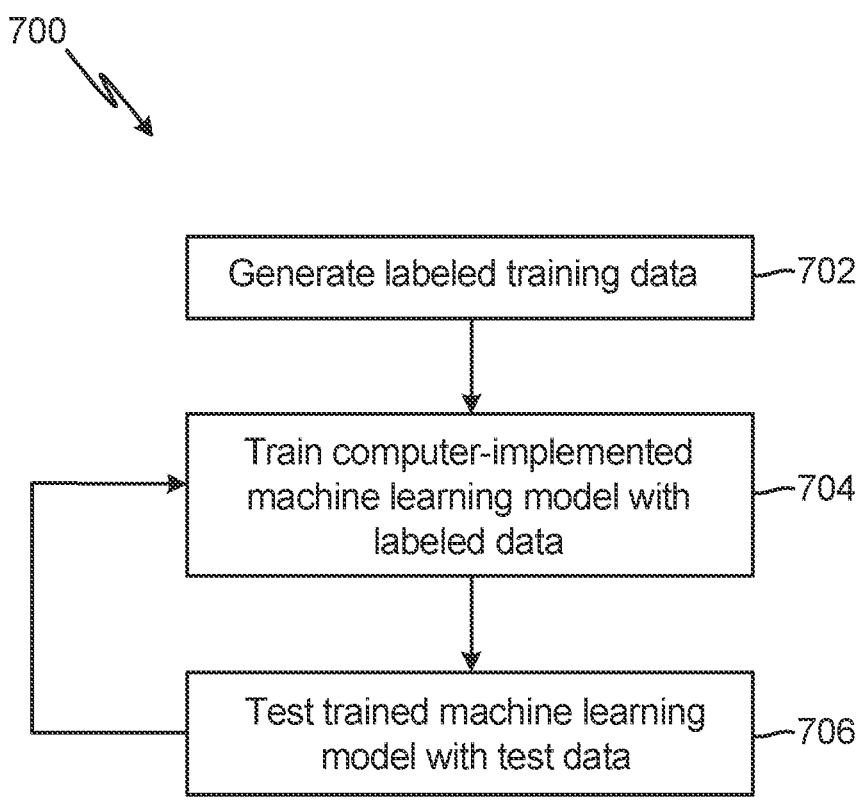
FIG. 7 is a flow diagram of an example of a method of training a computer-implemented machine learning model suitable for use with other methods of this disclosure.

FIG. 7 is a flow diagram of method 700, which is a method of training a computer-implemented machine learning model. Method 700 includes steps 702-706 of generating labeled training data (step 702), training the computer-implemented machine learning model with the labeled data (step 704), and testing the trained computer-implemented machine learning model with test data (step 706). Method 700 can be used to train any machine learning model described herein (e.g., for a machine learning model for predicting mental state values, for relating changes in mental state to actions, etc.), but will be discussed with respect to a generic machine learning model for explanatory purposes.

In step 702, labeled data is generated. The labeled data can be, for example, audio data, image data, semantic text data, or labeled outputs of another trained machine learning model. The data can be labeled according to the dimensions of the multidimensional mental state model used to predict the baseline mental state in step 220. For example, if the multidimensional mental state model used with methods 200 and 500 includes intensity and pleasantness dimensions, the labeled data used in step 702 can be labeled to include intensity and pleasantness values. Further, if the type of data is used to determine a particular subset of dimensions of the multidimensional mental state model, the labeled data used in step 702 can be labeled only values for those dimensions to improve model fit. For example, the multidimensional mental state model can include three dimensions of intensity, pleasantness, and importance, and audio data can be used to determine only values along the intensity and pleasantness dimensions. The labeled audio data used to train a machine learning model in step 702 can be labeled only with intensity and pleasantness values to improve fit of the machine learning model to the relevant intensity and pleasantness values with which the model is intended to be used.

In step 704, the labeled data is used to train the computer-implemented machine learning model. As used herein, "training" a computer-implemented machine learning model refers to any process by which parameters, hyper parameters, weights, and/or any other value related model accuracy are adjusted to improve the fit of the computer-implemented machine learning model to the training data.

In step 706, the trained computer-implemented machine learning model is tested with test data. The test data used in step 706 is unlabeled data that is used to qualify and/or quantify performance of the trained computer-implemented machine learning model. More specifically, a human or machine operator can evaluate the performance of the machine learning model by evaluating the fit of the model to the test data. Step 706 can be used to determine, for example, whether the machine learning model was overfit to the labeled data during model training in step 704.

As depicted in FIG. 7, steps 704 and 706 can be performed iteratively to improve the performance of the machine learning model. More specifically, if the fit of the model to the unlabeled data determined in step 706 is undesirable, step 704 can be repeated to further adjust the parameters, hyper parameters, weights, etc. of the model to improve the fit of the model to the test data. Step 706 can then be repeated with a new set of unlabeled test data to determine how the adjusted model fits the new set of unlabeled test data. If the fit continues to be undesirable, further iterations of steps 704 and 706 can be performed until the fit of the model becomes desirable.

The methods and systems disclosed herein advantageously allow for the training and use of machine learning models that can predict the mental state of an individual captured in video data. The methods and systems disclosed herein further advantageously allow for the generation of one or more actions that another, second individual can perform to adjust the mental state of the individual captured in the video data to improve task performance.

As described previously, the use of a multidimensional mental state model provides significant advantages over existing methods of determining mental state. Specifically, a multidimensional mental state model according to the present disclosure improves the accuracy of mental state predictions and the efficiency with which mental state predictions can be computed. Further, a multidimensional mental state model provides significant flexibility over other existing mental state models and provides improved granularity and resolution, thereby improving the accuracy of mental state predictions made using the multidimensional mental state model.

The methods and systems disclosed herein enable the automatic prediction of a baseline mental state of an individual performing a task or activity and the automatic generation of actions for adjusting mental state to improve task performance. Advantageously, the actions produced using the methods and systems disclosed herein provide actions for adjusting mental state, enabling performance improvement for tasks or activities where emulating the behavior of a proficient individual is unlikely to provide improvements to performance. Further, the actions produced using the methods and systems disclosed herein improve competency of a coach, teacher, and/or tutor seeking to help another individual improve performance at a particular task or activity.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the present disclosure.

The invention claimed is:

1. A method comprising:
acquiring video data of a first individual;
extracting image data and audio data from the video data;
extracting semantic text data from the audio data;
analyzing at least one of the image data, the audio data, and the semantic text data to identify a first set of features;
predicting a baseline mental state of the first individual based on the first set of features, wherein:
the baseline mental state comprises a first mental state value and a second mental state value;
the first mental state value corresponds to a first dimension of a multidimensional mental state model; and
the second mental state value corresponds to a second dimension of the multidimensional mental state model;
identifying a target mental state for the first individual, wherein:
the target mental state comprises a third mental state value and a fourth mental state value;
the third mental state value corresponds to the first dimension of the multidimensional mental state model; and
the fourth mental state value corresponds to the second dimension of the multidimensional mental state model;
simulating, by a simulator, a predicted path from the baseline mental state toward the target mental state using the multidimensional mental state model, a plurality of actions, and a first computer-implemented machine learning model, wherein:
the first computer-implemented machine learning model is configured to relate actions of the plurality of actions and changes in value in at least one of the first dimension and the second dimension of the multidimensional mental state model;
the predicted path comprises one or more actions of the plurality of actions and corresponding changes to at least one of the first dimension and the second dimension of the multidimensional mental state model; and
the one or more actions are performable by a second individual to adjust the baseline mental state of the first individual toward the target mental state; and
outputting an indication of the one or more actions to the second individual.

2. The method of claim 1, wherein:
the target mental state is identified based on a task performed by the first individual; and
the video data depicts the first individual performing the task.

3. The method of claim 1, wherein the one or more actions output to the second individual are for performing a second task different than the first task.

4. The method of claim 3, wherein performance of the second task causes the second individual to interact with the first individual.

5. The method of claim 1, wherein predicting the baseline mental state comprises:
generating, by a second computer-implemented machine learning model, the first mental state value based on the first set of features; and generating, by a third computer-implemented machine learning model, the second mental state value based on the first set of features.

6. The method of claim 5, wherein the first dimension describes an intensity of a first mental state and the second dimension describes a pleasantness of the first mental state.

7. The method of claim 5, wherein the first dimension describes an intensity of the first mental state, a pleasantness of the first mental state, an importance of information conveyed by the first individual, a positivity of the conveyed information, or a subject of the conveyed information.

8. The method of claim 5, wherein the first dimension describes a first mental state, the second dimension describes a second mental state, and the first mental state and the second mental state are selected from a group consisting of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and ennui.

9. The method of claim 1, wherein analyzing at least one of the image data, the audio data, and the semantic text data to identify the first set of features comprises:
analyzing the image data to identify the first set of features;
analyzing the to identify a second set of features; and
analyzing the semantic text data to identify a third set of features.

10. The method of claim 9, wherein predicting the baseline mental state comprises:
generating, by a second computer-implemented machine learning model, the first mental state value based on at least one of the first set of features, the second set of features, and the third set of features; and
generating, by a third computer-implemented machine learning model, the second mental state value based on at least one of the first set of features, the second set of features, and the third set of features.

11. The method of claim 9, wherein predicting the baseline mental state comprises:
generating, by a second computer-implemented machine learning model, the first mental state value based on the first set of features and the second set of features; and
generating, by a third computer-implemented machine learning model, the second mental state value based on the first set of features and the second set of features.

12. The method of claim 11, wherein:
the baseline mental state comprises a fifth mental state value corresponding to a third dimension of the multidimensional mental state model;
the target mental state comprises a sixth mental state value corresponding to the third dimension of the multidimensional mental state model;
the first computer-implemented machine learning model is configured to relate actions of the plurality of actions and changes in value in at least one of the first dimension, the second dimension, and the third dimension of the multidimensional mental state model; and
the predicted path comprises one or more actions of the plurality of actions and corresponding changes to at least one of the first dimension, the second dimension, and the third dimension of the multidimensional mental state model.

13. The method of claim 12, wherein predicting the baseline mental state further comprises generating, by a fourth computer-implemented machine learning model, the fifth mental state value based on the third set of features.

14. The method of claim 13, wherein the first dimension describes an intensity of a first mental state, the second dimension describes a pleasantness of the first mental state, and the third dimension describes an importance of information conveyed by the first individual.

15. The method of claim 14, wherein:
the second computer-implemented machine learning model is configured to relate intensity of the first mental state with features of the first set of features and the second set of features;
the third computer-implemented machine learning model is configured to relate pleasantness of the first mental state with features of the first set of features and the second set of features; and
the fourth computer-implemented machine learning model is configured to relate an importance of information conveyed by the first individual with features of the third set of features.

16. The method of claim 9, wherein analyzing the audio data to identify the second set of features comprises:
converting the audio data to a spectrogram; and
analyzing the spectrogram with a fourth computer-implemented machine learning model.

17. The method of claim 1, wherein the simulating the predicted path comprises:
generating a first plurality of intermediate points based on the changes in value in at least one of the first dimension and the second dimension and the baseline mental state, wherein each intermediate point of the first plurality of intermediate points corresponds to an action of the one or more actions;
measuring a first plurality of Euclidean distances between the first plurality of intermediate points and the target mental state;
determining a first preferred intermediate point of the first plurality of intermediate points, the first preferred intermediate point having a shortest Euclidean distance of the first plurality of Euclidean distances to the target mental state; and
storing, as a first step of the predicted path, the change in value in at least one of the first dimension and the second dimension used to generate the first preferred intermediate point and the corresponding action of the one or more actions.

18. The method of claim 17, wherein simulating the predicted path further comprises:
generating a second plurality of intermediate points based on the changes in value in at least one of the first dimension and the second dimension and the first preferred intermediate point, wherein each intermediate point of the second plurality of intermediate points corresponds to an action of the one or more actions;
measuring a second plurality of Euclidean distances between the second plurality of intermediate points and the target mental state;
determining a second preferred intermediate point of the second plurality of intermediate points, the second preferred intermediate point having a shortest Euclidean distance of the second plurality of Euclidean distances to the target mental state; and
storing, as a second step of the predicted path, the change in value in at least one of the first dimension and the second dimension used to generate the second preferred intermediate point and the corresponding action of the one or more actions.

19. The method of claim 1, wherein outputting the indication of the one or more actions to the second individual comprises:
   cross-referencing, with a table of actions and instructions, the one or more actions to determine one or more instructions for performing the one or more actions; and
   outputting the one or more instructions to the second individual.

20. A system for adjusting mental state, the system comprising:
   a processor;
   a user interface; and
   a memory encoded with instructions that, when executed, cause the processor to:
      acquire video data of a first individual;
      extract image data and audio data from the video data;
      extract semantic text data from the audio data;
      analyze at least one of the image data, the audio data, and the semantic text data to identify a first set of features;
      predict a baseline mental state of the first individual based on the first set of features, wherein:
         the baseline mental state comprises a first mental state value and a second mental state value;
         the first mental state value corresponds to a first dimension of a multidimensional mental state model; and
         the second mental state value corresponds to a second dimension of the multidimensional mental state model;
      identify a target mental state for the first individual, wherein:
         the target mental state comprises a third mental state value and a fourth mental state value;
         the third mental state value corresponds to the first dimension of the multidimensional mental state model; and
         the fourth mental state value corresponds to the second dimension of the multidimensional mental state model;
      simulate, by a simulator, a predicted path from the baseline mental state toward the target mental state using the multidimensional mental state model, a plurality of actions, and a first computer-implemented machine learning model, wherein:
         the first computer-implemented machine learning model is configured to relate actions of the plurality of actions and changes in value in at least one of the first dimension and the second dimension of the multidimensional mental state model;
         the predicted path comprises one or more actions of the plurality of actions and corresponding changes to at least one of the first dimension and the second dimension of the multidimensional mental state model; and
         the one or more actions are performable by a second individual to adjust the baseline mental state of the first individual toward the target mental state; and
      cause the user interface to output an indication of the one or more actions to the second individual.

* * * * *